(12) United States Patent
Probert et al.

(10) Patent No.: US 6,387,384 B1
(45) Date of Patent: May 14, 2002

(54) DISINFECTANTS TO ERADICATE VIRAL DISEASES SUCH AS HIV AND HEPATITIS

(76) Inventors: David D. Probert; Jacklyn O. Probert, both of 1209 W. 1520 N., Clinton, UT (US) 84015

( * ) Notice: Subject to any disclaimer, the term of this patent is extended or adjusted under 35 U.S.C. 154(b) by 0 days.

(21) Appl. No.: 09/471,223

(22) Filed: Dec. 23, 1999

(51) Int. Cl.[7] .................... A01M 25/34; A61K 33/14; A61K 9/70
(52) U.S. Cl. .................. 424/404; 424/661; 424/443
(58) Field of Search .................. 424/404, 401, 424/402, 78.1, 661, 443; 604/306; 422/28

(56) References Cited

U.S. PATENT DOCUMENTS

| | | | |
|---|---|---|---|
| 4,847,089 A | 7/1989 | Kramer et al. | 424/405 |
| 4,899,905 A | 2/1990 | Holtsch | 221/63 |
| 4,988,341 A * | 1/1991 | Columbus et al. | 604/306 |
| 4,990,334 A * | 2/1991 | Longino et al. | 424/401 |
| 5,087,450 A * | 2/1992 | Lister | 424/402 |
| 5,185,371 A * | 2/1993 | Rubinstein | 422/28 |
| 5,320,217 A | 6/1994 | Lenarz | 206/209 |
| 5,531,984 A | 7/1996 | Staats | 424/78.07 |
| 5,811,113 A * | 9/1998 | Dorr et al. | 424/404 |

* cited by examiner

Primary Examiner—Thurman K. Page
Assistant Examiner—Blessing Fubara
(74) Attorney, Agent, or Firm—Kirton & McConkie

(57) ABSTRACT

The present invention is directed to sodium hypochlorite solutions, solids, sprays, gels, powders and bandages to sanitize or disinfect against the harmful effects of diseases such as HIV or hepatitis.

8 Claims, 3 Drawing Sheets

DISINFECTANTS TO ERADICATE VIRAL DISEASES SUCH AS HIV AND HEPATITIS

BACKGROUND

1. Field of the Invention

The present invention is directed to devices, compositions and methods for disinfectants to eradicate viral diseases such as HIV and hepatitis and the like. In particular, the present invention is directed to applications of alcohols and/or bleaches in wipe, spray, paste, gel, powders or tablets, or bandage form.

2. Background Art

The background and field of this invention is related to disinfectants for cleaning and sanitizing working surfaces or surfaces of skin. Various forms of rubbing alcohol such as 70% isopropyl alcohol have long been used to prepare skin surfaces for health care treatments and procedures. For example, U.S. Pat. No. 4,899,905 teaches a container with a strip of continuous premoisturized swabs, each swab being rectangular and interconnected with adjacent swabs at their respective corners. The swabs are impregnated with an antiseptic such as alcohol. While rubbing alcohols are effective cleaners because of their highly volatile nature, alcohols are not effective disinfectants. On the other hand, some concentrations of hydrogen peroxide compositions have been used as disinfectants. For example, U.S. Pat. No. 4,847,089 teaches a sponge or wipe relying upon a quaternary ammonium hydro peroxide phase-transfer complex achieved by employing an aqueous solution of an alkaline water-soluble salt having hydrogen peroxide of crystallization and a positively charged phase-transfer agent. U.S. Pat. No. 5,531,984 teaches an antimicrobial composition having antiviral, antibacterial and antifungal properties and including a first quaternary ammonium compound, a second quaternary ammonium compound, a nonionic surfactant and a stabilizer. U.S. Pat. No. 5,087,450 teaches a virucidal wipe including a gauze impregnated with 10% sodium hypochlorite solution shielded by a flexible non-porous plastic barrier firmly attached to the gauze to protect the user from viral contamination and from the sodium hypochlorite. Similarly, U.S. Pat. No. 5,320,217 teaches towelettes in a metal foil package bearing germicides such as povidone-iodine, paints, paint removers, nail polish or remover, lubricants, solvents, adhesives and ointments.

However, the known prior art does not present a simple, effective, and readily portable mechanism for disinfecting harmful viruses such as HIV or hepatitis without exposing the user to caustic or corrosive substances and without the need for barriers and other protective devices.

BRIEF SUMMARY AND OBJECTS OF THE INVENTION

An object of the present invention is to provide a disinfectant effective to killing HIV and hepatitis without exposing the user to harmful disinfectants.

Another object of the present invention is to provide structures and methods for efficiently dispensing the new disinfectants of the present invention.

A still further object of the present invention is to provide a low concentration sodium hypochlorite solution for use as a disinfectant against HIV and hepatitis contamination.

A further object of the present invention is to provide a composition compromising sodium hypochlorite and alcohol for use as a disinfectant against HIV and hepatitis contamination.

Additional objects of the present invention is to provide delivery modalities including wipes, sprays and bandage applications.

Additional objects and advantages of the invention will be set forth in the description which follows, and in part will be obvious from the description, or may be learned by the practice of the invention. The objects and advantages of the invention may be realized and obtained by means of the instruments and combinations described below and particularly pointed out in the appended claims.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

The present invention maybe embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The present invention is directed to structures, methods and composition of disinfectants effective in sanitizing against diseases from HIV or hepatitis. The present invention is directed to compositions and mechanisms which are inexpensive to manufacture, convenient to use, portable and effective in sanitizing against the infective harms of HIV and hepatitis without the need of using physical barriers or protection to prevent contact with the skin of the user.

The present invention is directed to compositions and delivery of sodium hypochlorite solutions. In one embodiment, it has been discovered that small percentage weights of low concentration sodium hypochlorite have sufficient effectiveness in killing HIV and hepatitis viruses to be capable of delivery in a wipe or towelette modality without risking harm to the user from the HIV or hepatitis or from the sodium hypochlorite. For example, a composition of water comprising about 0.4 percent by weight 5.25% sodium hypochlorite has been shown effective for sanitizing surfaces contaminated with HIV or Hepatitis B. Using a 5.25% sodium hypochlorite, about 4.7 percent by weight water solution has been shown more effective to disinfect surfaces contaminated with HIV or Hepatitis B. At these concentrations, the compositions have shown no material or lasting harmful effect when applied directly to the skin. In other words, at these concentrations, there is no need for physical or chemical barriers to prevent contact with the skin of user because it is effective and safe.

It is contemplated that this composition can be delivered in a number of different modalities, including liquid, spray, paste, gel, powders, dehydrated tablet, or incorporated into liquid, solid or dry soaps, cleansers and cleaners. The preparation of pastes, gels, powders and dehydrated tablets of concentration taught by the present invention are readily known by those skilled in the art. It also contemplated that a paste, gel or solid modality may be preapplied to a wipe, gauze or adhesive bandages in effective quantities for ease and convenience of packaging, storage, portability and dispensing. For example, a small skin lesion associated with HIV can be effectively treated with a localized application. A localized application can be achieved using an adhesive bandage delivery modality.

Figure 1:
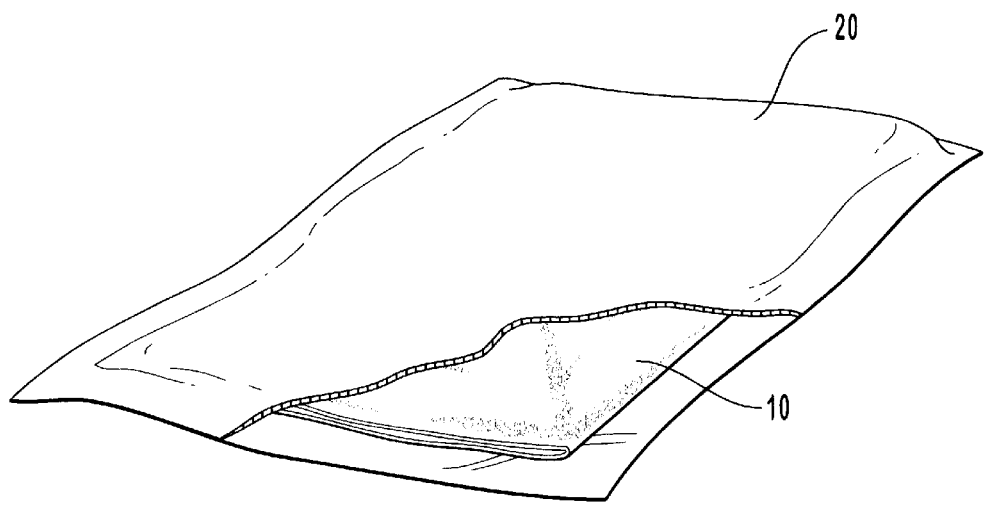
FIGS. 1 and 2 depict one embodiment of dispensing individual towelettes or wipes.
Figure 2:
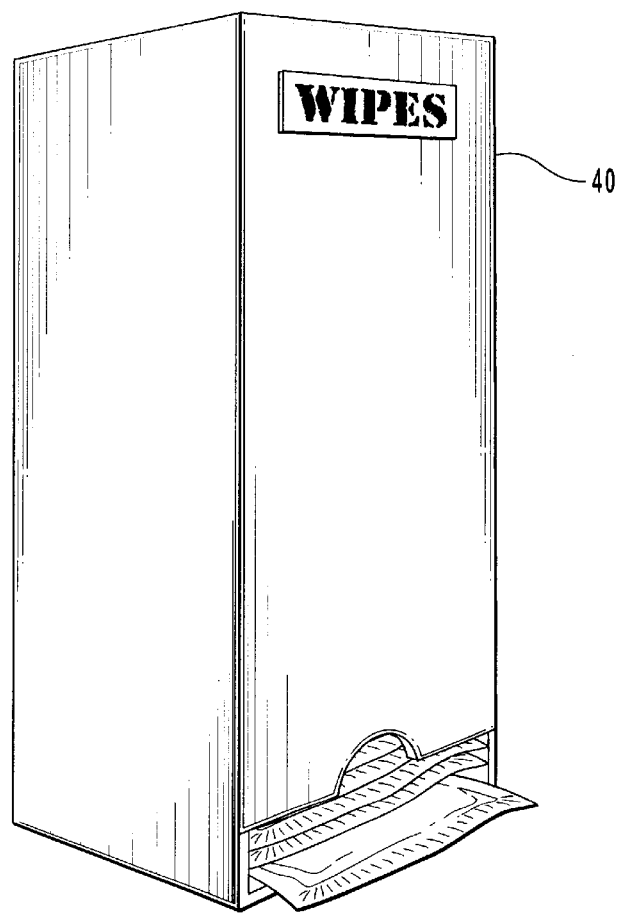
Figure 3:
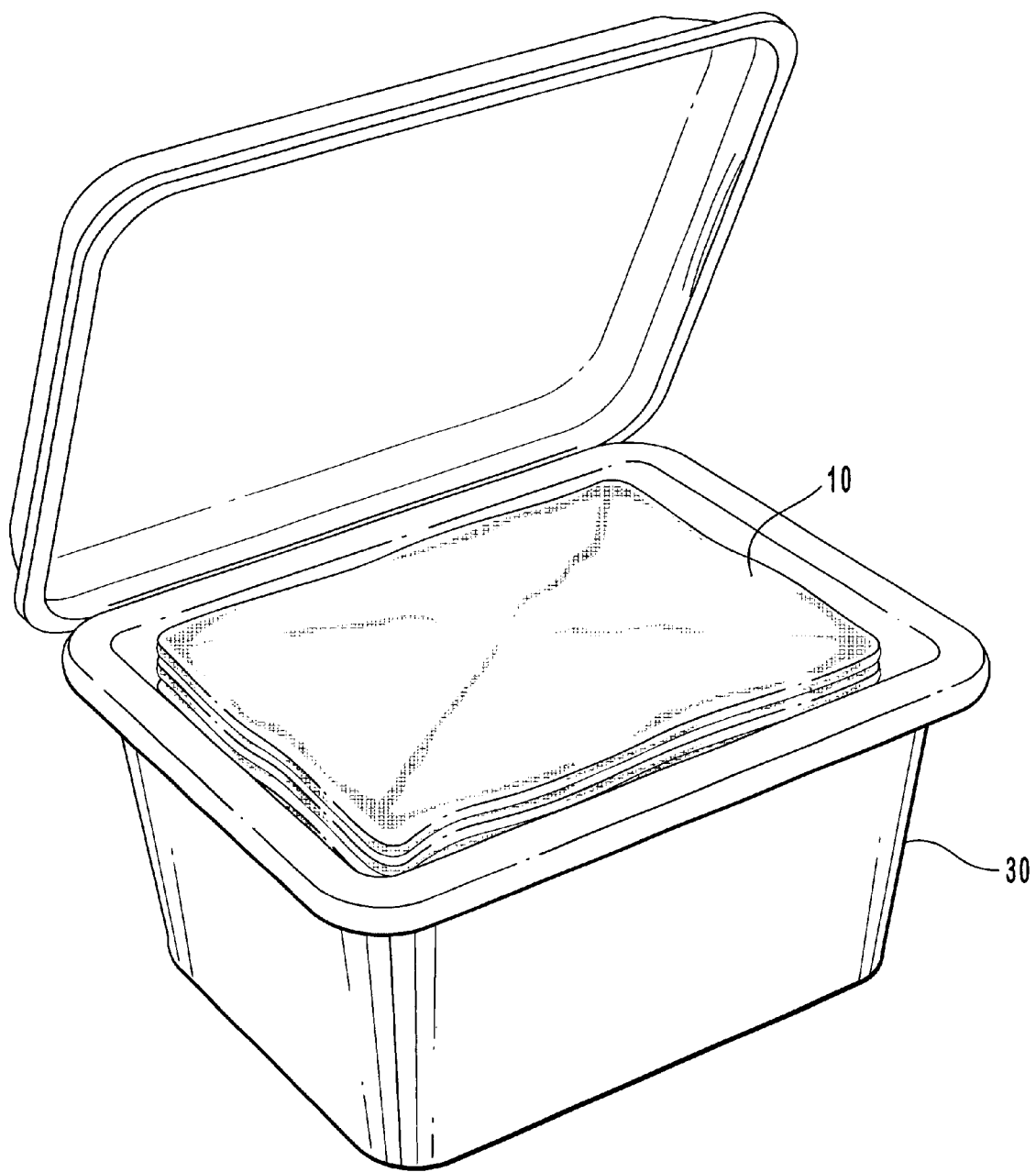
FIG. 3 depicts one embodiment of a container with multiple towelettes or wipes.
Figure 4:
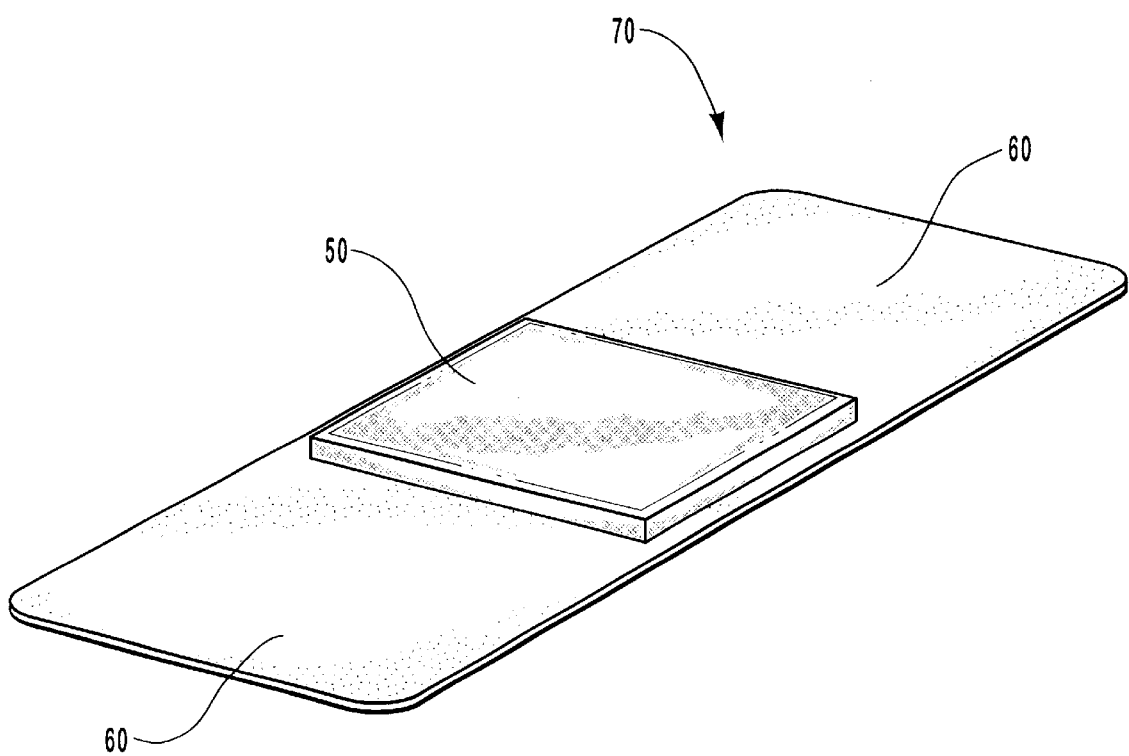
FIG. 4 depicts one embodiment of a bandage delivery system.

The wipe modality is shown in FIGS. 1–3. A towelette or wipe 10 is made available in either sealed, individual foil or plastic pouches 20 or in a stack in a tub 30. The individual pouches may be stored or offered from a dispenser 40. The bandage delivery may be accomplished using the bandage 70 of FIG. 4. Bandage 70 comprises a disinfectant host 50 for bearing the sodium hypochlorite and combination sodium hypochlorite-alcohol in the selected form, discussed below. Segments 60 may bear any suitable adhesive.

In another embodiment, another sanitizing agent is added to the sodium hypochlorite. In one embodiment, an alcohol is combined with the sodium hypochlorite such that the composition comprises a sodium hypochlorite portion and an alcohol portion. Isopropyl alcohol of 70% solution has been used as the alcohol portion. Depending on the percent concentration, other grades or commercial grades may be used. Testing and investigation has resulted in the conclusion that combinations of sodium hypochlorite and alcohol are sufficiently stable and are not chemically interactive so as to compromise the combined sanitizing and disinfecting properties of the compounds. This combination comprising a sodium hypochlorite portion and an alcohol portion may also be delivered in a number of different modalities, including liquid, spray, paste, gel, dehydrated tablet, or incorporated into liquid, solid or dry soaps, cleansers and cleaners. A paste, gel or solid modality of a combination may be preapplied to gauze or adhesive bandages in effective quantities for ease and convenience of packaging, storage, portability and dispensing. For example, a small skin lesion associated with HIV can be effectively treated with a localized application of the combination. A localized application can be achieved using an adhesive bandage delivery modality.

An inert perfume may be added as desired.

Examples of combinations comprising a sodium hypochlorite portion (5.25% concentration) and an alcohol portion (70% concentration) include the following different embodiments which were made by adding the compounds together in liquid form by adding the percentage weight sodium hypochlorite to the percentage weight isopropyl alcohol, and thereafter adding the stated percentage weights of water and perfume. All weights are in percentage weight of the combined composition:

EXAMPLE 1

| substance | % weight |
| --- | --- |
| sodium hypochlorite | .004 |
| isopropyl alcohol | 70.0 |
| water | 27.996 |
| perfume | 1.0 |

EXAMPLE 2

| substance | % weight |
| --- | --- |
| sodium hypochlorite | .008 |
| isopropyl alcohol | 70.0 |
| water | 27.992 |
| perfume | 1.0 |

EXAMPLE 3

| substance | % weight |
| --- | --- |
| sodium hypochlorite | .012 |
| isopropyl alcohol | 70.0 |
| water | 27.988 |
| perfume | 1.0 |

EXAMPLE 4

| substance | % weight |
| --- | --- |
| sodium hypochlorite | .015 |
| isopropyl alcohol | 70.0 |
| water | 27.985 |
| perfume | 1.0 |

EXAMPLE 5

| substance | % weight |
| --- | --- |
| sodium hypochlorite | .016 |
| isopropyl alcohol | 70.0 |
| water | 27.984 |
| perfume | 1.0 |

EXAMPLE 6

| substance | % weight |
| --- | --- |
| sodium hypochlorite | .023 |
| isopropyl alcohol | 70.0 |
| water | 27.977 |
| perfume | 1.0 |

EXAMPLE 7

| substance | % weight |
| --- | --- |
| sodium hypochlorite | .031 |
| isopropyl alcohol | 70.0 |
| water | 27.969 |
| perfume | 1.0 |

EXAMPLE 8

| substance | % weight |
|---|---|
| sodium hypochlorite | .047 |
| isopropyl alcohol | 70.0 |
| water | 27.53 |
| perfume | 1.0 |

EXAMPLE 9

| substance | % weight |
|---|---|
| sodium hypochlorite | .035 |
| isopropyl alcohol | 70.0 |
| water | 27.965 |
| perfume | 1.0 |

EXAMPLE 10

| substance | % weight |
|---|---|
| sodium hypochlorite | .062 |
| isopropyl alcohol | 70.0 |
| water | 27.938 |
| perfume | 1.0 |

In addition, the following combinations comprising a 5.25% sodium hypochlorite portion and a 70% isopropyl alcohol portion may be made as follows:

EXAMPLE 11

| substance | % weight |
|---|---|
| sodium hypochlorite | 0.19 |
| isopropyl alcohol | 70.0 |
| water | 27.981 |
| perfume | 1.0 |

EXAMPLE 12

| substance | % weight |
|---|---|
| sodium hypochlorite | 0.039 |
| isopropyl alcohol | 70.0 |
| water | 27.961 |
| perfume | 1.0 |

EXAMPLE 13

| substance | % weight |
|---|---|
| sodium hypochlorite | .058 |
| isopropyl alcohol | 70.0 |
| water | 27.942 |
| perfume | 1.0 |

EXAMPLE 14

| substance | % weight |
|---|---|
| sodium hypochlorite | .086 |
| isopropyl alcohol | 70.0 |
| water | 27.914 |
| perfume | 1.0 |

EXAMPLE 15

| substance | % weight |
|---|---|
| sodium hypochlorite | .07 |
| isopropyl alcohol | 70.0 |
| water | 27.93 |
| perfume | 1.0 |

EXAMPLE 16

| substance | %weight |
|---|---|
| sodium hypochlorite | .027 |
| isopropyl alcohol | 70.0 |
| water | 27.973 |
| perfume | 1.0 |

EXAMPLE 17

| substance | % weight |
|---|---|
| sodium hypochlorite | .043 |
| isopropyl alcohol | 70.0 |
| water | 27.957 |
| perfume | 1.0 |

EXAMPLE 18

| substance | % weight |
|---|---|
| sodium hypochlorite | .055 |
| isopropylcohol | 2.0 |
| water | 95.945 |
| perfume | 1.0 |

EXAMPLE 19

| substance | % weight |
|---|---|
| sodium hypochlorite | .094 |
| isopropyl alcohol | 89.0 |
| water | 8.906 |
| perfume | 1.0 |

EXAMPLE 20

| substance | % weight |
|---|---|
| sodium hypochlorite | .08 |
| isopropyl alcohol | 70.0 |
| water | 27.92 |
| perfume | 1.0 |

EXAMPLE 21

| substance | % weight |
|---|---|
| sodium hypochlorite | .002 |
| isopropyl alcohol | 70.0 |
| water | 28.998 |
| perfume | 1.0 |

EXAMPLE 22

| substance | % weight |
|---|---|
| sodium hypochlorite | .20 |
| isopropyl alcohol | 70.0 |
| water | 28.80 |
| perfume | 1.0 |

It will be understood by one of skill in the art that the sodium hypochlorite concentration may vary. Percentage weights of sodium hypochlorite of 5.25% concentration may vary from about 0.002% to about 0.2% with a corresponding increase in the percentage weight of alcohol and/or water. If concentration of sodium hypochlorite varies, so too would the corresponding percentage weights. Similarly, the isopropyl alcohol concentration may vary from about 20% to about 90%. Similarly, percentage weights of isopropyl alcohol may also vary from about 2% to about 89% with a corresponding increase in the percentage weight of water.

Other disinfectants may be added as desired with corresponding reductions in the percentage weights of the other substances. For example, germicides, aldehydes, iodophores, chlorhexidines, quats, or phenolics may be added as desired.

While the examples above are directed to liquid forms of the present invention, including a pump spray delivery, it is also contemplated that compositions of the present invention can also be delivered by aerosol delivery. This requires the use of propellant used with the compositions above under pressure. It is believed that use of isobutane, butane, propane or any other noninteractive propellant will provide an aerosol delivery modality that would permit spraying the sodium hypochlorite solution or combined sodium hypochlorite-alcohol composition on the surface to be sanitized or disinfected.

Minor modification or changes to weights and concentrations are within the spirit of this invention. The scope of the present invention is set forth in the appended claims.

What is claimed and desired to be secured by United States Patent is:

1. A disinfecting wipe for harmful contamination, comprising:
   a prepackaged towelette bearing sodium hypochlorite in a percentage weight from about 0.002% to about 0.2%.

2. A disinfecting wipe for harmful contamination, comprising:
   a prepackaged towelette bearing sodium hypochlorite in a percentage weight from about 0.002% to about 0.2% and an alcohol in a percentage weight from about 20% to about 90%.

3. A disinfecting spray for harmful contamination, comprising:
   a solution having sodium hypochlorite in a percentage weight from about 0.002% to about 0.2%.

4. The spray of claim 3 further comprising a propellant to deliver the solution under pressure.

5. A disinfecting spray for harmful contamination, comprising:
   a solution having sodium hypochlorite in a percentage weight from about 0.002% to about 0.2% and an alcohol in a percentage weight from about 20% to about 90%.

6. The spray of claim 5 further comprising a propellant to deliver the solution under pressure.

7. A disinfecting bandage, comprising:
   a prepacked bandage bearing sodium hypochlorite in a percentage weight from about 0.002% to about 0.2%.

8. A disinfecting bandage, comprising:
   a prepacked bandage bearing sodium hypochlorite in a percentage weight from about 0.002% to about 0.2% and an alcohol in a percentage weight from about 20% to about 90%.

* * * * *

UNITED STATES PATENT AND TRADEMARK OFFICE
CERTIFICATE OF CORRECTION

| | | |
|---|---|---|
| PATENT NO. | : 6,387,384 B1 | |
| DATED | : May 14, 2002 | |
| INVENTOR(S) | : David D. Probert and Jacklyn O. Probert | |

It is certified that error appears in the above-identified patent and that said Letters Patent is hereby corrected as shown below:

<u>Title page,</u>
Item [56], References Cited, add -- 5,575,993 A, * 11/1996, Ward et al., 424/78.1 --

<u>Column 2,</u>
Line 32, change "maybe" to -- may be --

Signed and Sealed this

Twelfth Day of November, 2002

*Attest:*

*Attesting Officer*

JAMES E. ROGAN
*Director of the United States Patent and Trademark Office*